US00PP09619P

United States Patent [19]

Endisch et al.

[11] Patent Number: Plant 9,619

[45] Date of Patent: Aug. 6, 1996

[54] GERANIUM PLANT NAMED 'NEILA'

[75] Inventors: Gerd Endisch, Geranienweg, D-76767, Hagenbach; Ursula Endisch-Burmeister, Bad Kreuznach, both of Germany; Wolf Endisch, Teneriffa, Spain

[73] Assignee: Gerd Endisch, Hagenbach, Germany

[21] Appl. No.: 384,143

[22] Filed: Feb. 6, 1995

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

P.P. 5,369 12/1984 Schumann ..... Plt./87.12
P.P. 7,494 4/1991 Klemm ..... Plt./87.12

*Primary Examiner*—James R. Feyrer
*Attorney, Agent, or Firm*—Willian Brinks Hofer Gilson & Lione

[57] ABSTRACT

A new and distinct cultivar of geranium known by the cultivar name 'Neila' is characterized by a rose colored flower, a semi-double flower form, dark foliage, early flower response, a compact habit and good heat tolerance.

1 Drawing Sheet

BACKGROUND OF THE NEW PLANT

The present invention comprises a new and distinct cultivar of geranium botanically known as *Pelargonium zonale,* and hereinafter referred to by the cultivar name 'Neila'.

'Neila' is a product of planned breeding program which had the objective of creating new geranium cultivars with rose flower color, semi-double flower form, dark foliage, early flower response.

'Neila' was originated from a hybridization made in a controlled breeding program in Hagenbach, Germany, in 1990. The female parent was 'Rica', characterized by its pink flower color, semi-double flower form, and light green foliage. 'Rica', which is available from Elsner PAC, is distinct from 'Neila' in that 'Neila' has darker foliage and a different flower color. The male parent of 'Neila' was 'Unica', characterized by its salmon-pink flower color, semi-double flower form, dark foliage without zonation, late flower response. 'Unica', which is no longer commercially available, differs from 'Neila' in that 'Neila' shows an earlier flower response, has a slight leaf zonation, is more compact, and has a different flower color.

Neila' was discovered and selected as one flowering plant within the progeny of the stated cross by the inventors in Aug. 1992 in a controlled environment in Hagenbach, Germany.

DESCRIPTION OF THE NEW PLANT

The first act of asexual reproduction of 'Neila' was accomplished when vegetative cuttings were taken from the initial selection in Jan. 1992 in a controlled environment in Hagenbach, Germany, by a technician working under formulations established and supervised by Gerd Endisch.

Horticultural examination of selected units initiated in May 1992 has demonstrated that the combination of characteristics as herein disclosed for 'Neila' are firmly fixed and are retained through successive generations of asexual reproduction.

'Neila' has not been observed under all possible environmental conditions. The phenotype may vary signficantly with variations in environment such as temperature, light intensity, and day length. The following observations, measurements, and comparisons describe plants grown in Hagenbach, Germany, under field conditions which approximate those generally used in commercial practice. The measurements and dimensions given below are approximate.

The following traits have been repeatedly observed and are determined to be basic characteristics of 'Neila' distinguish this geranium as a new and distinct cultivar:

1. rose flower color
2. semi-double flower form
3. dark foliage
4. early flower response
5. compact habit
6. good heat tolerance Of the many commercial cultivars known to the present inventors, there is no cultivar similar in comparison to 'Neila'.

BRIEF DESCRIPTION OF THE DRAWINGS

The accompanying photographic drawing show typical flower and foliage characteristics of 'Neila' with colors being as true as possible with illustrations of this type.

DETAILED BOTANICAL DESCRIPTIONS

In the following description color references are made to The *Royal Horticultural Society Colour Chart* (RHS). The color values were determined indoors from plants grown outdoors in Aug. 1994 in Hagenbach, Germany, or Hannover (Bundessortenamt).

Classification:

*Botanical.*—A hybrid of the species 'Pelargonium zolane.

*Commercial.*—Zonal geranium, cv. 'Neila'.

Inflorescence:

*Umbel.*—An umbel comprises approx. 35 flowers.

*Average diameter.*—Approx. 95 mm.

*Average depth.*—Approx. 53 mm.

*Peduncle length.*—Approx. 145–150 mm.

*Spring flowering response period.*—In Hannover (Bundessortenamt) first flower 8 Apr. 94; 50% of plants with at least one flower opened 13 weeks after planting of unrooted cuttings.

*Outdoor flower production.*—The flower count in 1993 indicated between 65–70 flowers per plant for May 15 through Aug. 15 observation period.

*Durability: Good rain resistance. Good heat resistance.*

Corolla:

*Average diameter.*—Approx. 48–50 mm.

*Form.*—Semi-double.

*Color.*—(General tonality from a distance of three meters) rose pink.

*Color of petals (top surface).*13RHS 68B: upper and lower petals are substantially solid pink; upper petals may contain lighter spots in the center of varying hues to near white.

*Color of petals (bottom surface).*—RHS 68 C.

*Pedicel length.*—Approx. 32 mm.

*Pedicel color.*—Light red (anthocyanin colored).

*Petaloids.*—None.

*Persistence.*—Non-shattering flower.

Bud:

*size.*—Approx. 1.4–1.8 cm across.

*Shape.*—Ovoid.

*Color.*—Light green with anthocyanin at the base.

*Sepals.*—Five, pointed linear lanceolate; at time of petal appearing approx. 12 mm in length.

Reproductive Organs:

*Stamens.*—Anthers: 7–10 in number. Filaments: Approx. 6–8 mm in length. Pollen: Orange— red in color.

*Pistil.*— No.: 1 Length: Approx. 9mm. Stigma: 5 lobes. Style: Approx. 3mm in length; color: red.

*Ovaries.*—Green.

*Fruit.*—Partially fertile.

Plant:

*Foliage.*—Abundant quantity. Size: Approx. 10.0–11.5 cm across. Shape: Reniform in plan. Margin: Bicrenate. Texture: Lightly pubescent. Ribs and veins: Palmate venation. Color (upper surface): Dark green, RHS 137 A. Color (zonation): Light zonation, green, RHS 147 A. Color (bottom surface): RHS 137 B to 137 C. Petioles: Approx. 8–10 cm in length; green.

*General appearance and form.*—Bushy, compact habit. Internode length: Approx. 19 mm. Branching pattern: 18 branches observed 15 Aug. 94. Height: Approx. 19–21 cm from media surface. Strength: Early flower response and good heat tolerance.

What is claimed is:

1. A new and distinct cultivar of geranium plant known as 'Neila' as described and illustrated and particularly characterized by a rose colored flower, a semi-double flower form, dark foliage, early flower response, a compact habit and good heat tolerance.

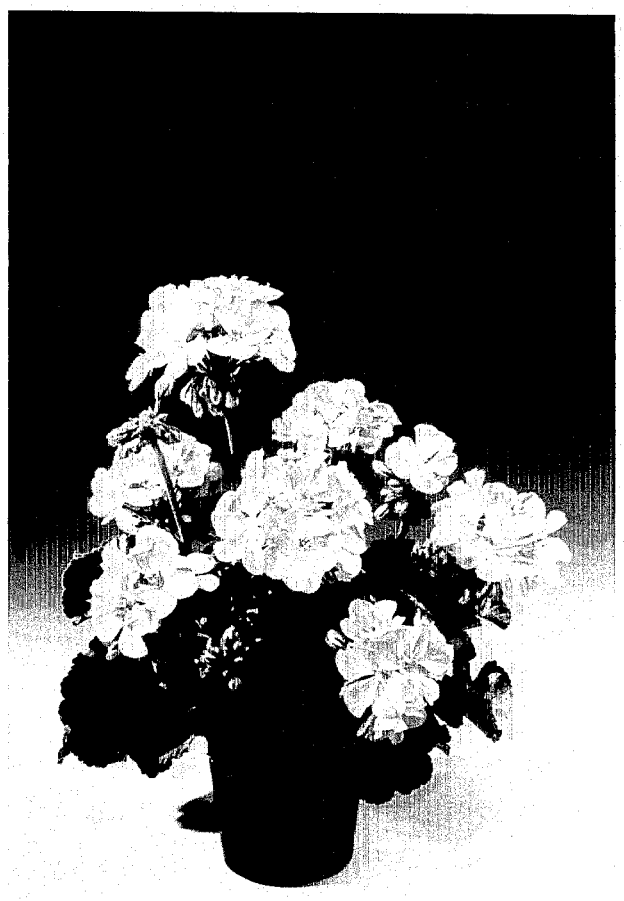

* * * * *